US00PP20508P2

(12) United States Plant Patent
Danziger

(10) Patent No.: US PP20,508 P2
(45) Date of Patent: Nov. 24, 2009

(54) ***TORENIA* PLANT NAMED 'DANLOV196'**

(50) Latin Name: *Torenia sp.*
Varietal Denomination: DANLOV196

(75) Inventor: Gabriel Danziger, Moshav Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.

(21) Appl. No.: 12/283,876

(22) Filed: Sep. 16, 2008

(51) Int. Cl.
*A01H 5/00* (2006.01)

(52) U.S. Cl. ..... Plt./487

(58) Field of Classification Search ..... Plt./487
See application file for complete search history.

*Primary Examiner*—Annette H Para
(74) *Attorney, Agent, or Firm*—Foley & Lardner LLP

(57) ABSTRACT

A new and distinct *Torenia* plant named 'DANLOV196' particularly characterized by plenty of delicate, funnel form, cup- shaped flowers with petals in shades of purple-violet, violet and violet-blue with a yellow blotch on lower petal; cascading bush, which maintains a compact, rounded plant habit; vigorous growth habit; densely branched plant, gracefully cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.

Variety denomination: 'DANLOV196'.

BACKGROUND OF THE INVENTION

The present invention relates to a new and distinct cultivar of *Torenia* plant, botanically known as *Torenia* sp. of the Scrophulariaceae family, and hereinafter referred to by the cultivar name DANLOV196.

The new *Torenia* is a product of a planned breeding program conducted by the inventor, Gabriel Danziger, in Moshav Mishmar Hashiva, Israel. The objective of the breeding program was to develop a new *Torenia* with unique petal coloration.

The new *Torenia* originated from a cross made in a controlled breeding program by the inventor, Gabriel Danziger, in 2004 in Moshav Mishmar Hashiva, Israel. The female or seed parent is the *Torenia* cultivar designated 'TR 118' (unpatented) The male or pollen parent is the *Torenia* cultivar designated 'TR 112' (unpatented). The new *Torenia* cultivar was discovered and selected by the inventor, Gabriel Danziger, as a single flowering plant within the progeny of the stated cross in a controlled environment in April of 2005 in Moshav Mishmar Hashiva, Israel.

Asexual reproduction of the new *Torenia* cultivar by soft cuttings was first performed in May of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANLOV196' which in combination distinguish this *Torenia* as a new and distinct cultivar:

1. Plenty of delicate, funnel form, cup-shaped flowers with petals in shades of purple-violet, violet and violet-blue with a yellow blotch on lower petal;
2. Cascading bush, which maintains a compact, rounded plant habit;
3. Vigorous growth habit;
4. Densely branched plant, gracefully cascading from hanging baskets;
5. Early flowering response and stays in full bloom in moderate climate;
6. Suitable as an annual for hanging pots outdoors under partial shade; and
7. Good weather tolerance with a preferred temperature range of 15° C. to 25° C.

Plants of the new *Torenia* 'DANLOV196' differ from plants of the parents, 'TR 118' (unpatented) and 'TR 112' (unpatented) in the characteristics described in Table 1.

TABLE 1

| Characteristic | New Cultivar 'DANLOV196' | Female Parent 'TR 118 (unpatented) | Male Parent 'TR 112' (unpatented) |
|---|---|---|---|
| Mature Flower color | Petal shades of purple-violet, violet and violet-blue, with a yellow blotch on lower petal | Petal shades of blue, with no yellow blotch on lower petal | Petal shades of light blue, with a yellow blotch on lower petal |
| Flower size | Depth: About 3 cm Width: About 2.5 cm | Depth: About 2.5 cm Width: About 3 cm | Depth: About 3.5 cm Width: About 3 cm |
| Growth habit | Cascading bush | Trailing | Cascading bush |
| Flowering Response Time | 7 weeks from planting | 8 weeks from planting | 9 weeks from planting |

Of the many commercial cultivars known to the present inventor, the most similar in comparison to the new *Torenia*

'DANLOV196' is the *Torenia* 'DANTOMOON10' (patented, U.S. Plant Pat. No. 17,009), in the characteristics described in Table 2:

TABLE 2

| Trait | New Cultivar 'DANLOV196' | Comparison Cultivar 'DANTOMOON10' (patented) |
|---|---|---|
| Mature Flower Color | Petal shades of purple-violet, violet and violet-blue, with a yellow blotch on lower petal | Petal shades of light violet blue and violet, with a yellow blotch on lower petal |
| Flower size | Depth: About 3.0 cm Width: About 2.5 cm | Depth: About 3.8 cm Width: About 3.0 cm |
| Growth habit | Cascading bush | Cascading bush |
| Flowering Response Time | 7 weeks from planting | 5 weeks from planting |

BRIEF DESCRIPTION OF THE PHOTOGRAPHS

The accompanying photographs illustrate the overall appearance of the new *Torenia* 'DANLOV196' showing the colors as true as is reasonably possible with colored reproductions of this type. Colors in the photographs may differ slightly from the color values cited in the detailed botanical description, which accurately describe the color of 'DANLOV196'.

DETAILED BOTANICAL DESCRIPTION

Figure 1:
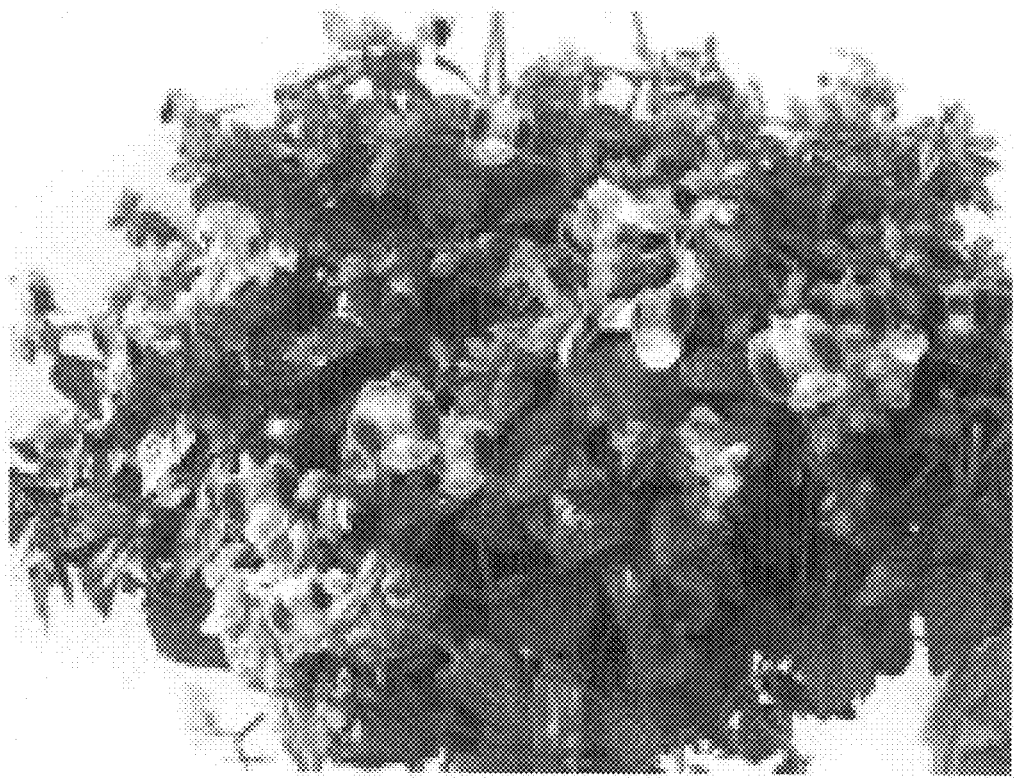
FIG. 1 shows a side perspective view of a typical flowering plant of 'DANLOV196' in a hanging planter at 2 months of age.
Figure 2:
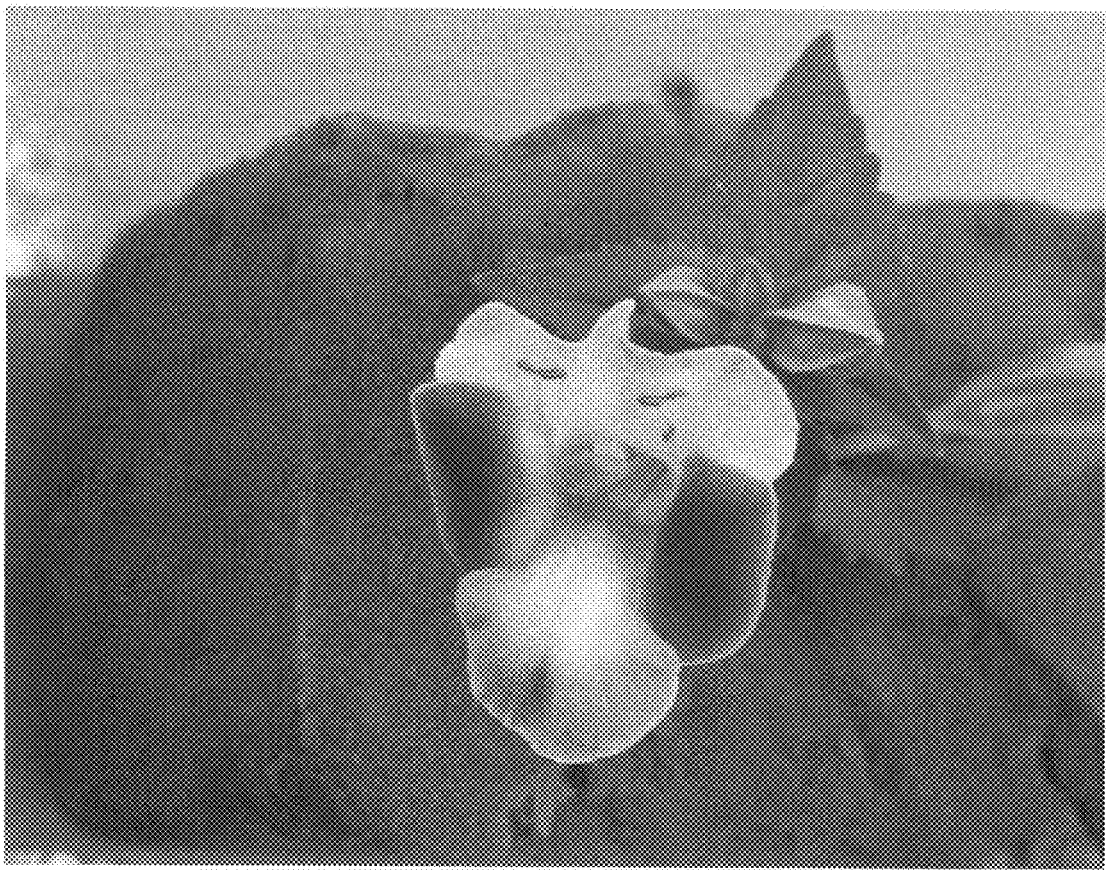
FIG. 2 shows a close-up of the typical flowers, buds and leaves of 'DANLOV196' at 2 months of age.

The new *Torenia* 'DANLOV196' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANLOV196' as grown in a greenhouse in Moshav Mishmar Hashiva, Israel, under conditions which closely approximate those generally used in commercial practice. Optimal growth conditions include that plants of 'DANLOV196' are grown outdoors in a moderate climate and indoors during the winter season. Irrigation and fertilization are recommended on a regular basis. Plants of 'DANLOV196' are usually grown in full sunlight, but partial shade is required in mid summer. Plants of 'DANLOV196' are fully grown in 2 months from planting a cutting in the summer season and bloom all year-round in a moderate climate. The 'DANLOV196' plants described herein were grown indoors in 13 cm pots in a glass greenhouse in Moshav Mishmar Hashiva, Israel, with the day temperatures ranging from 18° C. to 35° C. and night temperatures ranging from 16° C. to 25° C. Plants of 'DANLOV196' were fertilized up to a level of 59 ppm N, 35.4 ppm P and 94.4 ppm K.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANLOV196' plants described is 7 weeks.

Parentage:

*Female or seed parent.*—*Torenia* cultivar designated 'TR 118' (unpatented).

*Male or pollen parent.*—*Torenia* cultivar designated 'TR 112' (unpatented).

Propagation: Tissue culture and soft tip cuttings.

Plant:

*Form.*—Bush, cascading.

*Growth habit.*—Rounded.

*Height.*—About 25 cm.

*Spread.*—40 cm to 60 cm.

*Cold tolerance.*—Frost tender. Temperatures below 5° C. may damage plants.

*Vigor.*—Vigorous growth; plants are fully grown in 2 months from planting cutting in during summer season.

Stem:

*Color.*—Yellow-Green, RHS 144A.

*Length.*—About 30 cm.

*Diameter.*—About 3 mm.

*Pubescence.*—Minimal.

*Branching.*—About 15 to 35 main branches grow from the base and split into hundreds of secondary and tertiary branches.

*Length of internodes.*—2 to 8 cm.

Foliage:

*Overall shape.*—Deltoid.

*Apex.*—Acute.

*Base.*—Cordate.

*Size of leaf.*—Width: 1.5 cm to 3.5 cm Length: About 2 cm to 4 cm.

*Margin.*—Serrate.

*Color (mature).*—Center color of leaf: Green, RHS 137A Upper side: Green, RHS 137A Under side: Green, RHS 138B.

*Color (immature).*—Center color of leaf: Green, RHS 138A Upper side: Green, RHS 138A Under side: Green, RHS 138B.

*Leaf texture.*—Upper: Glabrous with sensible veins Under: Glabrous with sensible veins.

*Venation.*—Pattern: Anastomotic Color: Upper surface: Yellow-Green, RHS 150C Lower surface: Green, RHS 143C.

*Petioles.*—Length: About 0.2 cm to 0.6 cm Diameter: About 1.0 mm Color: Green, RHS 143C.

Flowers:

*Blooming period.*—All year round in a moderate climate or in a greenhouse environment. In Israel, flowering occurs between March and November outdoors.

*Flowering response time.*—About 7 weeks from planting.

*Flowering stem.*—Flowers appear along the growing stems.

*Quantity of flowers.*—Per stem: About 5 to 8;. Per plant: About 120 to 180.

*Flowering longevity.*—On the plant: about 2 to 5 days, depending on temperature.

*Type.*—Single.

*Shape.*—Overall: funnel form; 5-winged; Corolla tube: cylindrical or often broadened above; Corolla: 2-lipped, the upper lip faintly 2-lobed, the lower lip 3-lobed.

*Orientation at opening.*—Slanted upward.

*Fragrance.*—None.

*Flower size.*—Depth: About 3.0 cm Width: About 2.5 cm.

*Bud.*—Shape: Oblong, cylindrical, ellipsoid, 5-winged Size: Length: About 1.5 cm Diameter: About 7.0 mm.

*Color.*—Apex: Yellow-Green, RHS 144A Base: Yellow-Green, RHS 144A.

*Texture.*—Pubescence on winged edges.

*Floral tube.*—Length: About 2.5 cm Width: About 0.5 cm to 1.3 cm Color: Outside: Purple-Violet, RHS N82B (apex), Yellow-Orange, RHS 18C (middle) and Yellow, RHS 11D (base). Inside: Purple-Violet, RHS N82C (apex) and Yellow, RHS 13A (base).

*Petals.*—Number: Four, fused. Length: Upper Petal: About 1.6 cm; Side Petals: About 2.0 cm; Lower Petal: About 1.3 cm. Width: Upper Petal: About 2.5 cm; Side Petals: About 1.0 cm; Lower Petal: About 1.7 cm. Shape: Upper Petal:Overall: spatulate, Apex: rounded, Base: fused; Side Petals: Overall: spatulate, Apex: rounded, Base: fused; Lower: Overall: spatulate, Apex: rounded, Base: fused. Margin: Undulated and toothed. Color: Mature Petals: Upper Surface: Upper Petal: Near apex, Purple-Violet, RHS N82A, and near base, Violet-Blue, RHS 91C; and margin, Purple-Violet, RHS N82A; Side Petals: Violet: Near apex, RHS N87A, with centralized RHS N87A, and near base, RHS N87B, and margin RHS N87B; Lower Petal: Primarily Violet-Blue, RHS 91A, with Yellow, RHS 4B blotch in the middle near base, and Violet-Blue, RHS 91C color surrounding blotch and near base, and margin, Violet-Blue, RHS 91C. Lower Surface: Upper Petal: Violet-Blue: Near apex, RHS 92B, and near base, RHS 92B and margin, RHS 92C; Side Petals: Near apex, Violet, RHS N87A, and near base, Violet-Blue, RHS 92C and Violet-Blue, margin, RHS 92C; Lower Petal: Violet-Blue: Near apex, RHS 91B, and near base, RHS 91C and margin, RHS 91C. Throat: Upper throat: Violet, RHS 85B; Lower throat: Violet, RHS 85A. Immature Petals: Upper Surface: Upper Petal: Near apex, Violet-Blue, RHS 92D, and near base, Violet-Blue, RHS 92D; and margin, Violet, RHS 86B; Side Petals: Violet, Near apex, RHS 86A, near base, RHS 86A, and margin RHS 86C; Lower Petal: Primarily Violet-Blue, RHS 91C, with Yellow, RHS 4C blotch in the middle near base, and margin, Violet, RHS N88C. Lower Surface: Upper Petal: Violet-Blue: Near apex, RHS 92D, and near base, RHS 92C and margin, RHS 92A; Side Petals: Violet-Blue: Near apex, RHS 93B, and near base, RHS 92C, and margin, RHS 92C; Lower Petal: Violet-Blue: Near apex, RHS 92D, and near base, RHS 92D and margin, RHS 92C; Throat: Center of Flower: Violet-Blue, RHS 92B.

*Sepals.*—Number: 5 Length: About 1.5 cm Width: About 0.8 cm Shape: Two-lobed, 5-winged Apex: Acute Base: Wedge shaped Margin: Undulated Color: Green, RHS 143C.

*Peduncle.*—Length: About 1.5 cm to 3.0 cm Diameter: About 2.0 mm Color: RHS 143B.

Reproductive organs:

*Androecium.*—Stamen: Number: 2 pairs per flower, fused Color: Violet-Blue, RHS 91D Anther: Length: About 0.3 cm; Width: About 1.0 mm Color (mature): Grey-Brown, RHS 199A Spur: Not Present Filament: Length: About 1.2 cm; upper anther shorter — about 0.3 cm Width: About 1.0 mm Color: Violet-Blue, RHS 91D Pollen: Amount: Sparse. Color: Grey-Brown, RHS N155D Requirements for pollination: Young flowers, active pollen, and receptive, open stigma.

*Gynoecium.*—Pistil: Number: One per flower Length: About 2.4 cm Stigma: Length: About 0.2 cm Width: About 0.2 cm Color: White, RHS N155B Style: Length: About 1.8 cm Color: White, RHS N155C Ovary: Number: 1 Length: About 0.4 cm Width: About 0.2 cm Color: Green, RHS 143B.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANLOV196', as illustrated and described herein.

* * * * *